United States Patent [19]

Arkel et al.

[11] Patent Number: 5,766,869
[45] Date of Patent: Jun. 16, 1998

[54] FACTOR V RATIO BLOOD TEST FOR SUSCEPTIBILITY TO THROMBOEMBOLISM

[75] Inventors: Yale S. Arkel, Westfield; Dehui Wayne Ku, Mt. Laurel, both of N.J.

[73] Assignee: AHS Hospital Corp., Summit, N.J.

[21] Appl. No.: 757,926

[22] Filed: Nov. 27, 1996

Related U.S. Application Data

[60] Provisional application No. 60/007,815, Nov. 30, 1995.

[51] Int. Cl.$^6$ .............................. C12Q 1/56; C12Q 1/37; G01N 33/53
[52] U.S. Cl. .................... 435/13; 435/23; 435/24; 435/4; 435/975; 435/214; 424/529; 424/530; 436/71; 436/63; 530/380; 530/381
[58] Field of Search ..................... 435/13, 23, 24, 435/4, 975, 214; 424/529, 530; 530/380, 381

[56] References Cited

U.S. PATENT DOCUMENTS

| | | | |
|---|---|---|---|
| 4,948,724 | 8/1990 | Yin | 435/13 |
| 5,051,357 | 9/1991 | Hassouna | 435/13 |
| 5,059,525 | 10/1991 | Bartl et al. | 435/13 |
| 5,169,786 | 12/1992 | Carroll et al. | 436/69 |
| 5,418,141 | 5/1995 | Zweig et al. | 435/13 |
| 5,439,802 | 8/1995 | Rosen | 435/13 |
| 5,443,960 | 8/1995 | Dahlback | 435/13 |
| 5,453,370 | 9/1995 | Triplett et al. | 435/214 |
| 5,472,850 | 12/1995 | Morrissey | 435/13 |
| 5,472,852 | 12/1995 | Smirnov et al. | 435/13 |
| 5,525,478 | 6/1996 | Matschiner | 435/13 |

FOREIGN PATENT DOCUMENTS

| | | |
|---|---|---|
| 9102812 | 3/1991 | WIPO. |
| 9417415 | 8/1994 | WIPO. |
| 9521938 | 8/1995 | WIPO. |
| 9615457 | 5/1996 | WIPO. |

OTHER PUBLICATIONS

Bjorn Dahlback, Molecular genetics of Thrombophilia: J. Lab Clin Med., vol. 125, No. 5, pp. 566–571, May 1995.

Dzung The Le, et al., Rapid Communication, Blood, vol. 85, No. 7, pp. 1704–1711, Apr. 1, 1995.

Majerus, News and Views, Bad Blood By Mutation, vol. 369, pp. 14–15, May 5, 1994.

Varadi, et al. British Journal of Haematology, A Chromogenic Assay for Activated Protein C Resistance, pp. 884–891, Apr. 28,1 995.

Hans de Ronde, et al., Thrombosis and Haemostasis, pp. 880–886, Sep. 8, 1994, Laboratory Diagnosis of APC-Resistance: "A Critical Evaluation of the Test and the Development of Diagnostic Criteria".

Bertina, et al., Mutation in Blood Coagulation Factor V Associate with Resistance to Activated Protein C, Nature vol. 369, 1994), pp. 64–67, Month not available.

Svensson, et al., Resistance to Activated Protein C As A Basis for Venous Thrombosis, The New England Journal of Medicine, vol. 330, No. 8, pp. 518–522, (Feb. 24, 1994.

(List continued on next page.)

*Primary Examiner*—Louise Leary
*Attorney, Agent, or Firm*—Allen N. Friedman

[57] ABSTRACT

The disclosed Factor V Ratio (FVR) screening blood assay (read as "factor five ratio") and kits for the conduct thereof, identify individuals that possess a specific genetic defect, known as the Factor V Leiden defect, or other genetic or acquired Factor V defect, that makes those individuals susceptible to venous thromboembolism. In this test the Factor V activity of a blood plasma sample exposed to activated Protein C (APC) is compared to the Factor V activity of a similar sample in the absence of APC, after both samples had been treated with an activating agent. The ratio between the Factor V activity level without APC and the Factor V activity level with APC, identifies individuals at risk of a thrombotic disorder due to a Factor V defect and differentiates between individuals with a heterozygous defect and individuals with a homozygous defect.

15 Claims, 2 Drawing Sheets

OTHER PUBLICATIONS

Rosendaal, et al., High Risk of Thrombosis in Patients Homozygous for Factor V Leiden (Activated Protein C Resistance), Blood, vol. 85, No. 6, pp. 1504–1508, Mar. 15, 1995.

Dahlback, Molecular Genetics of Venous Thromboembolism, Ann Med 27, pp. 187–192, 1995, Month not available.

Nachman, et al., Hypercoagulable States, 1993 Annals of Internal Medicine, vol. 119, (1993) pp. 819–826, Month not available.

De Stefano, et al., Clinical Manifestations and Management of Inherited Thrombophilia, Haemostasis, pp. 352–358, (1994) Month not available.

Beutler, et al., Williams Hematology, Fifth Edition, The Hypercoagulable State, pp. 1529–1542, (1995) Month not available.

Chromogenix, Coatest APC Resistance–C, Aug. 1995,Kit Data Sheet.

Tosetto, Thrombosis & Haemostasis, vol. 73 (1995) pp. 732–733.

Luddington, et al., British Journal of Hematology, vol. 92, (1996), p. 744, Month not available.

Kerschenbaum, Thrombosis and Haemostasis, vol. 75, (1996) p. 520, Month not available.

Kerschenbaum, et al., Thrombosis and Haemostasis, vol. 74 (1995), pp. 874–878, Month not available.

5,766,869

FACTOR V RATIO BLOOD TEST FOR SUSCEPTIBILITY TO THROMBOEMBOLISM

PRIORITY

This Application claims priority from Provisional Application #60/007815, filed Nov. 30, 1995 now abandoned.

BACKGROUND OF THE INVENTION

1. Field of the Invention

The invention is in the field of diagnostic blood testing.

2. Brief Description of the Background Art

Blood coagulation depends on a complex system of interlinked enzymes, proenzymes and cofactors, sometimes referred to as the clotting cascade, performing their roles at the surface of endothelial cells and platelets that have been activated by injury. In the absence of such activation these blood factors coexist in a dynamic balance that prevents the soluble blood fraction fibrinogen from forming fibrin that would crosslink to form an insoluble clot. This clotting system, its constituents and interactions are set forth in detail by Stefan Rosen in U.S. Pat. No. 5,439,802, issued Aug. 8, 1995. Any unbalance in this system can result in an individual being susceptible to uncontrolled bleeding (hemophilia) or spontaneous clot formation (thrombophilia).

Recent work by several groups has recognized a familial thrombophilia characterized by poor anticoagulant response to exogenous activated protein C (APC). An article reviewing this work was recently published by Bjorn Dahlbäck (Journal of Laboratory Clinical Medicine, Vol. 125 (1995) Pp. 566–571). The cause of this abnormal APC resistance was identified as an abnormality in the interaction of APC and Factor V in the blood stream. Factor V, in its normal and activated forms, is an essential part of the clotting mechanism. Activated protein C cleaves activated Factor V molecules, destroying their coagulant activity, thus helping to maintain the balance between the coagulant and anticoagulant influences in normal, undamaged blood vessels. Individuals with Factor V that is abnormally resistant to APC cleavage are susceptible to clot formation in undamaged blood vessels, thromboembolism. The above mentioned article also reviews attempts to formulate blood assays to screen for this deficiency.

In blood from normal individuals the clotting response to the Activated Partial Thromboplastin Time (APTT) test is prolonged in response to exogenously added APC because APC cleaves, among other factors, activated Factor V (Factor Va), destroying its coagulant activity. It has been shown that in many thrombophilic individuals the Factor Va molecule has a genetic defect that renders it abnormally resistent to APC cleavage. This genetic defect is referred to as the Factor V Leiden (FVL) defect. The cause of the defect has been identified as a mutation on the Factor V gene, resulting in substitution of Gln for Arg506 in the Factor V protein. It has been reported to be present in approximately one out of twenty individuals of the general Caucasian population of Europe and North America. It has been found in 25% to 50% of patients experiencing venous thromboembolism.

Dahlbäck also reports development of a screening assay for APC resistance, based on the observed failure of APC to appropriately prolong the time of clot formation in the APTT test. The test indicator is the clotting time ratio when the APTT test is performed with and without inclusion of APC in the clotting sample. This assay is referred to as the APCR assay. The incidence of the FVL mutation in patients with a positive result of the APCR test was reported to be 94% among the tested population of thrombotic individuals. Because of the lack of a complete correlation between this APCR screening clotting test of APC resistance and the FVL mutation, it was postulated that there may be other mechanisms for APC resistance. Reports of the clotting assay being effected by the presence of lupus inhibitor (LI) antibodies, with resultant ratios indicating APC resistance, raised the issue of induced resistance due to the LI antibodies or possibly the non-specific effect of the LI antibodies on phospholipid dependent coagulation tests (i.e., APTT tests). Tosetto, et. al. in later work (Thrombosis and Haemostasis, Vol. 73 (1995), Pp. 732–733) reported that the addition of factor V depleted plasma to the aPTT test system did a great deal to compensate for the above variables, making the test results more reflective of the presence of the FVL mutation.

Dzung The Le, et al. (Blood, Vol 85, No. 7 (1995) Pp. 1704–1711) report on an APC-resistance assay based on a tissue factor test specifically directed to measurement of Factor V coagulant activity. In the test used for this assay (disclosed in U.S. Pat. No. 5,169,786, issued Dec. 8, 1992), a diluted test plasma is incubated with a Factor V-deficient plasma and a tissue factor reagent containing thromboplastin. Equal samples (aliquots) are then clotted with $Ca^{2+}$ or $Ca^{2+}$ and APC. Le measured the clotting time difference in a series of tests as a function of plasma dilution and was able, by careful analysis, to differentiate between FVL-positive and FVL-negative (normal) individuals. His results were relatively unaffected by anticoagulant treatment or the presence of LI antibodies. However, there is still need for a test that is simple to conduct and has increased sensitivity and specificity for detection of the FVL defect.

SUMMARY OF THE INVENTION

The disclosed Factor V Ratio (FVR) screening blood assay (read as "factor five ratio") identifies individuals that possess a specific genetic defect, known as the Factor V Leiden defect, other Factor V genetic defects, or an acquired defect of the Factor V molecule, that makes those individuals susceptible to venous thromboembolism. In this test the Factor V activity of a blood plasma sample exposed to activated Protein C (APC) is compared to the Factor V activity of a similar sample in the absence of APC, after both samples had been treated with an activating agent. The ratio between the Factor V activity level without APC to the Factor V activity level with APC identifies individuals with a Factor V defect and differentiates between individuals with a heterozygous defect and individuals with a homozygous defect. Anticoagulant therapy is administered to individuals with a Factor V defect prior to surgery, child birth, or other circulatory system risk situations. The disclosed blood test kits include sets of reagents specifically standardized and normalized for conducting the FVR assay by either a coagulation method or a chromogenic method, identifying patients at risk of a thrombotic disorder due to a Factor V defect.

Prior assays, seeking to identify individuals susceptible to thromboembolism, have been sensitive to anticoagulant treatment and the presence of lupus inhibitor and/or anti-cardiolipin antibodies. We have addressed this issue by formulating an assay based on the tissue factor-based test for Factor V activity. This test can be performed easily and economically in the clinical coagulation laboratory. The assay indicator produced by this novel assay, the Factor V Ratio (FVR) assay, is expressed as the ratio of the Factor V activity without APC to the Factor V activity with the addition of APC. The Factor V activity of each sample can be determined by measuring clotting time by a standard coagulation method or by measuring the color change produced by the enzymatic activity of Factor V by a standard chromogenic method. While a Factor V-based method was reported by Le et al. (Blood, Vol 85 (1995) Pp. 1704–1711), in our FVR assay we incorporate an initial step of incubating the test plasma with a phospholipid/contact activator reagent, such as a commercial aPTT reagent, prior to measuring Factor V activity. This produces an assay that is 100% specific and sensitive for detection of the Factor V mutation.

We also compared the sensitivity and specificity of the FVR assay of the present invention to the two Activated Partial Thromboplastin Time (aPTT) methods, APCR and APCM. The APCR assay is the method described by Dahlback et al, and incorporated in the commercially available Coatest test kit (Chromogenix, Inc.). The APCM assay is an aPTT based method with the addition of Factor V depleted plasma to the test system. The data indicate that the novel FVR assay of the present invention is 100% specific and sensitive for detection of the FVL mutation. In contrast, the APCR and APCM tests showed overlapping test results for normal patients and patients possessing a Factor V defect. In addition, they could not reliably distinguish between patients with a homozygous defect and patients with a heterozygous defect. Further, when compared with tissue factor based Factor V assays without phospholipid, the FVR assay of the present invention is also more sensitive and specific for detection of a Factor V defect.

Expression of the test result as the Factor V activity ratio eliminates many test artifacts and the initial phospholipid treatment amplifies the sensitivity of the ratio indicator, activating Factor V to FVa and enhancing APC degradation of FVa. The FVR assay is not affected by anticoagulation treatment or the presence of anticardiolipin/lupus inhibitor antibodies. In the tested patient population, the FVR assay results completely correlated with the results of genetic testing for the FVL defect and differentiated completely and distinctly between individuals with a homozygous and a heterozygous defect. The method of the present invention also identifies individuals having other inherited Factor V defects or acquired defects of the Factor V molecule.

DETAILED DESCRIPTION OF THE INVENTION

Patients and Methods

Figure 1:
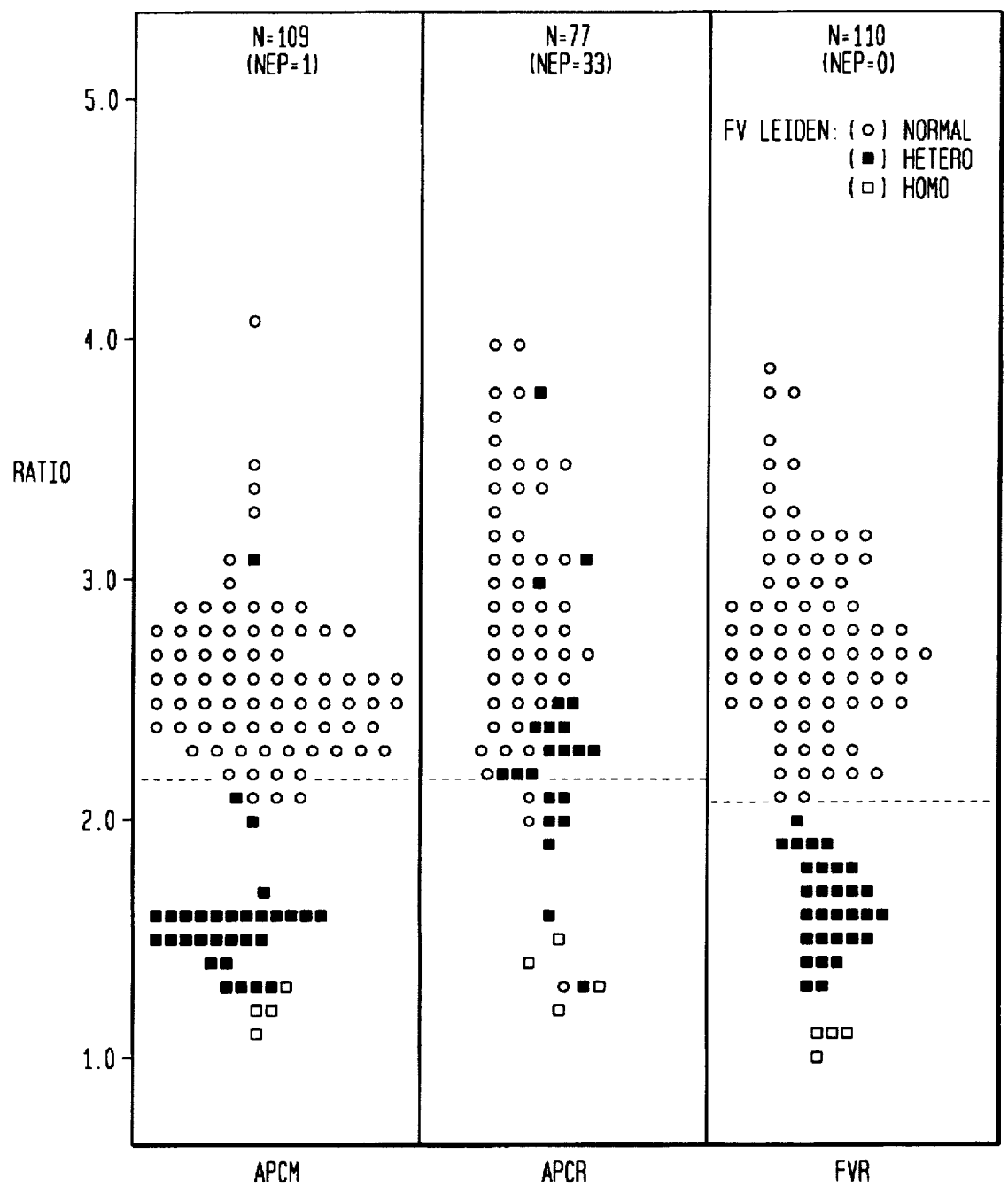
FIG. 1 is a chart showing the result of APCM ratio, APCR ratio and FVR ratio measurements on 110 subjects. In each column, NEP indicates how many samples are not reported because of No End Point reached, and the dotted line indicates the lower reference range of test results when the plasma from a 25 individual normal control population was tested.

The plasma samples submitted for study were obtained from patients referred to the Blood Disorder Center/ Overlook Hospital in Summit, N.J. for evaluation of a thrombotic disorder or patients having a family history of thrombotic disease. Seven additional plasma samples from patients with the FVL defect, documented by polymerase chain reaction (PCR) genetic testing, were obtained from the Pittsburgh Reference Alliance Laboratory. Control samples were obtained from 25 FVL negative individuals, as determined by PCR. They were healthy individuals with no history of thrombotic disease. A total of 110 patients, all of whom were tested for FVL using the PCR technique, were included in the study. Fifty nine of 110 (54%) of the patients had a history of venous thromboembolism. Nineteen of the 59 patients (32%), were FVL positive, possessing the Factor V Leiden defect. Seven of the 19 patients were receiving coumadin, one of the 19 was receiving heparin, and three of the 19 were receiving both coumadin and heparin. Of the total 110 patients, 19 tested positive for lupus inhibitor (LI) and/or anticardiolipin (ACL) antibodies and were FVL negative (Factor V normal). Five of the 110 patients tested positive for LI/ACL antibodies and the FVL defect (FVL positive). One of these five was receiving coumadin and heparin anticoagulation therapy. Nineteen of 110 patients were receiving coumadin and were FVL negative. Five of 110 patients were FVL negative and were receiving heparin. Two of the 110 patients were FVL negative and were receiving both coumadin and heparin.

Reagents

Human APC was purchased from Enzyme Research Laboratories, South Bend, Ind. Automated APTT™ (rabbit brain phospholipid with micronized silica as an activator), $CaCl_2$ (0.023 m/l ), Factor V Deficient Plasma, and Simplastin EXCEL™ were obtained from Organon Teknika, Durham N.C. Coatest APC kite was obtained from Chromogenix, Sweden. Pathromtin™ APTT reagent (Lipid extract from placentas with kaolin as activating agent) and Kaolin solution (5 g/l of kaolin in saline solution) were obtained from Behring Diagnostic Inc. Platelet lysate was obtained from America Diagnostic Company. SynthASIL™ aPTT (synthetic phospholipid with silica as an activator) reagent was obtained from Hemoliance Corp. of Raritan, N.J.

Methods

The plasma samples of all the patients and control subjects were subjected to three methods for detection of APC resistance. Two methods are based on an aPTT system (APCR and APCM) and the FVR method based on a ratio of tissue factor assays of factor V coagulant activity were evaluated.

The two methods we label APCR (i.e., APC ratio) and APCM (i.e., modified APC ratio) are based on an aPTT test, which use a phospholipid/contact activator reagent and coagulate with the addition of either $CaCl_2$ or $CaCl_2$ plus APC. This test uses standard tests available commercially, for example, as the Chromogenix Coatest™ test. The ratio of coagulation times with and without APC is the test result. The ratio of plasma to diluent in the test plasma samples is not critical. The clotting time is scaled to the concentration. Lower plasma concentrations result in longer clotting times. This property is used to adjust the clotting times to fall within the recommended operating range of the test instrument used. At the selected concentration, the test is standardized with respect to normal pooled plasma or plasma from a control group of normal individuals.

In the APCM method, Factor V depleted plasma in an amount at least equal to the test plasma is added in order to increase the specificity of the test to differences among the patients in Factor V activity response to APC. This method is based on work first published by Tosetto, et. al. (as referenced above).

In the novel assay described here, the test plasma is first incubated with a reagent containing phospholipid and a contact activator, such as micronized silica or kaolin. The phospholipid should be included in an amount from 0.25 to 75 micrograms per 100 microliter portion. Other contact activators such as celite and ellagic acid are also available. Suitable phospholipids include phosphatidyl choline, phosphatidyl ethanolamine, and phosphatidyl serine. These compounds can be naturally derived or synthetic. After addition of APC to one of two aliquots of test plasma and incubation of the two aliquots,the Factor V coagulant activity of the two samples is measured. The ratio of the Factor V coagulant activities of the two test samples, normalized against the Factor V activity of pooled normal plasma, is then calculated and used as the assay indicator. The test results were based on observation of clotting time, with clotting initiated by addition of $CaCl_2$ in the presence of Factor V deficient plasma and thromboplastin. In the alternative, chromogenic assays that can be used to detect Factor V enzymatic activity related to coagulation are available. These assays are based on color changes produced by reaction of a chromogenic substrate with a serine protease, such as thrombin or Factor Xa, produced in the clotting cascade. Such chromogenic testing can also be employed in the FVR assay. Such testing involves addition of a reagent containing the chromogenic substrate and a thromboplastin reagent without $CaCl_2$. The thromboplastin initiates the chemical reactions of the extrinsic clotting pathway involving Factor V. These chemical reactions produce the serine protease compounds that react with a chromogenic substrate (e.g., one of the Immunochrome series of chromogenic substrates produced by ImmunoAG of Vienna Austria) specifically designed to react with one of such compounds.

TEST INSTRUMENTATION

The clotting time measurements and chromogenic color change measurements used in the FVR assay are performed on equipment common to hospital laboratories. Thus, the FVR assay disclosed here can be easily and economically fit into a hospital's hemostasis testing program. The Behring Fibrintimer, produced by the Behring Diagnostics, Inc. of San Jose, Calif. and the ACL3000+ Automatic Coagulation Laboratory, produced by Instrumentation Laboratories of Lexington, Mass. were used to produce the test results that follow. The Behring Fibrintimer is a clot measuring device. The ACL 3000+ test instrument measures clotting time and also has facilities for chromogenic color change measurement. Each blood measurement instrument comes from the manufacturer with detailed standardization and normalization procedures.

Several reagents are used in the conduct of any particular blood test. While it is possible to purchase these reagents separately, it is common to purchase a set of reagents (a reagent kit) for each test from a single reagent manufacturer. The manufacturer will adjust the reagent concentrations to be compatible with the requirements of the particular test and will provide the parameters, curves and directions needed to standardize the test results. Instrument manufacturers and reagent manufacturers cooperate in making sure that the test kits and test instruments are compatible so that the entire measuring system will pass regulatory licensing requirements.

METHODS IN DETAIL

I. The FVR Assay

The FVR assays were performed on an ACL 3000+ Automatic Coagulation Laboratory test instrument. In this assay, data from testing of the patients' samples were compared to a standard curve. These tests used Simplastin Excels and Factor V deficient plasma from Organon Teknika. Control Factor V normal and Factor V deficient plasmas, obtained from George King Biomedical, Inc., were utilized for normalization. The clotting time was converted to percent activity utilizing a standard curve generated in accordance with instructions from the manufacturer of the test instrument. Many test instruments, for example the ACL 3000+ Automatic Coagulation Laboratory, are supplied with software that automatically generates the standard curve from data produced by running the test on standardized plasma samples.

The FVR ratio, was obtained using two aliquot samples of test platelet poor plasma run in parallel. The test mixtures consisting of 100 µl of test plasma and 100 µl of phospholipid reagent containing micronized silica obtained as AutoAPTT Reagent™ from Organon Teknika. These mixtures were incubated at 37° C. for 5 min. After incubation, 0.5 µl of distilled water was added to one sample and 0.5 µl of APC (1.18 mg/ml) to the other. Both samples were incubated for 2 min at 37° C. At the completion of incubation, 250 µl of Factor Diluent (Instrumentation Laboratory) was added to both samples, producing a 1:4.5 dilution, and the Factor V assays were performed as described above. The results were expressed as a ratio of the percent Factor V coagulant activity of the untreated sample and the percent Factor V coagulant activity of the APC treated sample. Normal pooled plasmas were run together with patient samples, and the FVR ratio was normalized against the normal pooled plasmas.

II. The APCR Assay

The APCR assay utilizes the standard commercially available Coatest™ as obtained from Chromogenix. The result is expressed as a ratio of the aPTT clotting time of the APC treated plasma sample to the aPTT clotting time of the untreated sample, the APCR ratio.

III. The APCM Assay

The APCM assay is a modification of the APCR assay. In the APCM assay, the Factor V deficient plasma is added to the patient plasma before the addition of APC. The clotting times are measured and the APCM ratio calculated as in the APCR assay.

TEST PROCEDURES

TEST I

TITLE: Activated Protein C (APC) Ratio in Behring Fibrintimer A (BFA)

PRINCIPLE: Plasma is incubated with aPTT reagent without $CaCl_2$ for a standard period of time. Coagulation is initiated by the addition of $CaCl_2$ in the absence and presence of APC and the time for clot formation is recorded. The test used is marketed by Chromogenix as the Coatest™ test. Clotting times were measured in the Behring Fibrintimer A.

SPECIMEN REQUIREMENTS: Platelet poor plasma, prepared from whole blood collected in 3.8% sodium citrate (9:1 ratio) by two syringe technique or in vacutainer tubes and kept on wet ice. Centrifuge at 4° C., 3000 g, for 20 minutes with Millex-GS filter from Millipore. Separate plasma from cells within two hours of collection. If the sample could not be tested immediately after preparation, it was frozen at −80° C. for up to three months.

Two samples were run in separate tubes. In both samples, 75 μl of patient's platelet poor plasma and 75 μl of APTT reagent from Chromogenix were mixed and the samples were incubated at 37° C. for 3 min. After 3 min, 75 μl of $CaCl_2$ (0.025 mol/l) from Chromogenix was added to one sample and 75 μl of $CaCl_2$ (0.025 mol/l) with APC to the other sample. The clotting time, up to 150 sec, was measured and the test results expressed as the clotting time ratio of APC treated/untreated samples.

INSTRUMENTATION: Behring Fibrintimer A (BFA)
Reagents:
CHROMOGENIX $CaCl_2$
CHROMOGENIX aPTT reagent-phospholipid plus silica contact activator
CHROMOGENIX APC/$CaCl_2$
CHROMOGENIX Normal Control plasma
CHROMOGENIX Abnormal Control plasma
Behring Wash Solution
REAGENT PREPARATION:
CHROMOGENIX $CaCl_2$—Ready for use. 8 ml of calcium chloride, 0.025mol/l concentration. Stable up to 1 month at 2°–8° C.
CHROMOGENIX aPTT—Ready for use. 16.5 ml of synthetic phospholipid with colloidal silica as contact activator. Stable up to 1 month at 2°–8° C. Avoid freezing, and mix carefully on a Cortex mixer before use.
CHROMOGENIX APC/$CaCl_2$—Reconstitute with 2.0 ml sterile water. Allow to stand 20 minutes and mix gently before use. Stable up to 2 hours at 37° C., 8 hours at room temperature and 5 days at 2°–8° C.
CHROMOGENIX Normal Control plasma—Reconstitute each vial with 1.0 ml sterile water. Allow to stand at room temperature for 20 MINUTES. Swirl gently before use. Stable up to 2 hours at +20° C. and 6 hours at 2°–8° C.
CHROMOGENIX Abnormal Control plasma—Reconstitute two vials each with 0.5 ml sterile water. Allow to stand at room temperature for 20 minutes. Swirl gently before use. Stable up to 2 hours at +20° C. and 6 hours at 2°–8° C.
Behring Wash Solution—use as is. Stable at room temperature till expiration date.
METHOD: Prepare two samples consisting of 75 μl of patient plasma and 75 μl of aPTT reagent from Chromogenix. Incubate both samples at 37° C. for 3 minutes. After 3 minutes, add 75 μl of $CaCl_2$ (0.025 mol/l) to one sample and 75 μl of $CaCl_2$ (0.025 mol/l) with APC to the other sample. Measured the clotting time up to 150 seconds.
CALCULATIONS $$\frac{\text{clot time } APC/CaCl_2}{\text{clot time } CaCl_2} = APC \text{ Ratio}$$

REFERENCE RANGE: The manufacturer's normal range is 2.0 to 5.0. Our normal range obtained in 25 health controls with negative PCR for Factor V Leiden was 2.2 to 3.4. We consider a value equal to or greater than 2.2 as being considered normal.
LIMITATIONS OF THE PROCEDURE:
The aPTT time should be within the normal range. The manufacturer warns that plasma samples showing prolonged aPTT times due to deficiencies in intrinsic coagulation factors, Lupus inhibitor and coagulation factor antibodies will have a false result. The manufacturer also warns that individuals to be investigated should not be on heparin or vitamin K antagonist therapy.

TEST II

TITLE: Modified APC Ratio in Behring Fibrintimer A (BFA)

PRINCIPLE: The APCM Ratio test is a modification of the Activated Protein C Ratio test (Test I). In this test Factor V deficient plasma is added to the patient diluted plasma and APTT reagent before the addition of activated protein C. Because of the dilution of the sample and the addition of Factor V deficient plasma, the reliability of the test result as an FVL indicator is enhanced for those patients on oral anticoagulants and those with lupus inhibitor/anticardiolipin antibodies.

SPECIMEN REQUIREMENTS: Platelet poor plasma, prepared from whole blood collected in 3.8% sodium citrate (9:1 ratio) by two syringe technique or in vacutainer tubes is kept on wet ice. Centrifuge at 10° C., 3000 g, for 20 minutes with Millex-GS filter from Millipore. Separate plasma from cells by pipetting within two hours of collection. If the sample could not be tested immediately after preparation, it was frozen at −80° C. for up to three months.

INSTRUMENTATION: Behring Fibrintimer A (BFA)
Reagents:
Organon Teknika $CaCl_2$
Organon Teknika Auto APTT reagent-phospholipid plus silica contact activator
Organon Teknika Factor V Deficient Plasma
Enzyme Research Laboratories APC
CHROMOGENIX Normal Control plasma
CHROMOGENIX Abnormal Control plasma
Behring Wash Solution
V Factor Diluent from Instrumentation Laboratories
REAGENT PREPARATION:
Organon Teknika $CaCl_2$—Ready for use. 10 ml of calcium chloride, 0.025mol/l concentration. Stable up to 1 month at 2°–80° C.
Organon Teknika Auto APTT reagent—Reconstitute with 6 ml distilled water. Stable up to 24 hours at 2°–8° C.
Enzyme Research Laboratories APC/$CaCl_2$—Add 10.5 μl of APC (1.18 mg/ml) to 5 ml calcium chloride, 0.025 mol/l. Stable up to 2 hours at 37° C., and 2 hours at 2°–8° C.
CHROMOGENIX Normal Control plasma—Reconstitute each vial with 1.0 ml sterile water. Allow to stand at room temperature for 20 minutes. Swirl gently before use. Stable up to 2 hour at +20° C. and 6 hours at 2°–8° C.
CHROMOGENIX Abnormal Control plasma—Reconstitute two vials each with 0.5 ml sterile water. Allow to stand at room temperature for 20 minutes. Swirl gently before use. Stable up to 2 hours at +20° C. and 6 hours at 2°–8° C.
Behring Wash Solution—use as is. Stable at room temperature till expiration date.
Instrumentation Laboratories Factor Diluent—use as is. Stable at room temperature till expiration date.
METHOD: Prepare two samples, each sample containing 50 μl of a 1:20 dilution of patient plasma with Instrumentation Laboratories Factor Diluent, 50 μl of AUTOAPTT reagent, and 50 μl of Factor V deficient plasma. Incubate the samples at 37° C. for 3 minutes. After 3 minutes, add 50 μl of CaCl$_2$ (0.025 mol/l) to one sample and 50 μl of CaCl$_2$ (0.025 mol/l) with APC (2.5 ug/ml) to the other sample. Measured the clotting time up to 250 seconds.

CALCULATIONS $$\frac{\text{clot time } APC/CaCl_2}{\text{clot time } CaCl_2} = APCM \text{ Ratio}$$

REFERENCE RANGE: The range obtained in 25 health controls with a negative polymerase chain reaction (PCR) for Factor V Leiden was 2.2 to 3.0. A value equal to or greater than 2.2 was considered normal.

LIMITATIONS OF THE PROCEDURE: Our data show that this test can give false positive and false negative results.

TEST III

TITLE: FACTOR V RATIO ASSAY (FVR) IN ACL 3000+ TESTER

PRINCIPLE: Patients with the mutation in the Factor V gene known as Factor V Leiden (FVL), have an increased tendency to venous thrombosis. A characteristic of this mutant form of Factor V is its decreased ability to be degraded by Activated Protein C (APC). Widely used tests using the activated Partial Thromboplastin Time (aPTT) system have demonstrated the above abnormality. This is done by comparing the clotting times of plasma treated with APC to a non treated specimen. The FVR method is based on a comparison of the Factor V coagulant activity with and without exposure of the test plasma to activated protein C. In this assay, the test plasma is first treated with a reagent containing a phospholipid and a contact activator. After incubation for 5 minutes at 37° C. an aliquot of test plasma is treated with APC, this is incubated for 2 minutes at 37° C. and then Factor V assays of the treated and untreated aliquots are performed in the ACL 3000+ test instrument, with the addition of Factor V deficient plasma and using Simplastin Excel to initiate clotting. This latter reagent contains CaCl$_2$. The ratio of the Factor V coagulant activity level of the untreated over the Factor V coagulant activity level of the APC treated sample is the FVR ratio.

The advantage of this method compare to aPTT based tests are:

1. Greater specificity for detection of the FVL defect.
2. Unaffected by use of anticoagulants (Coumadin or Heparin).
3. Unaffected by presence of lupus inhibitor/anticardiolipin antibodies.

SPECIMEN REQUIREMENTS: Platelet poor plasma, prepared from whole blood collected in 3.8% sodium citrate (9:1 ratio) by two syringe technique or in vacutainer tubes is kept on wet ice. Centrifuge at 4° C., 3000 g. for 20 minutes with Millex-GS filter from Millipore. Separate plasma from cells by pipetting within one hour of collection. If the sample could be tested immediately after preparation, It was frozen at −80° C. for up to three months.

INSTRUMENTATION: ACL 3000+ Automatic Coagulation Laboratory test instrument from Instrumentation Laboratories of Lexington, Mass.

REAGENTS:

Organon Teknika Auto aPTT phospholipid/silica reagent—phospholipid plus contact activator Organon Teknika Factor V Deficient Plasma Organon Teknika Simplastin Excel—thromboplastin with CaCl$_2$ Instrumentation Laboratories calibration Plasma Factor Frozen Pooled Normal Plasma (George King Fact)

Factor Frozen Pooled Abnormal Plasma median range Factor V deficiency(George King B Fact)

Enzyme Research Laboratories APC (1.18 mg/ml)

Instrumentation Laboratories Factor diluent

Instrumentation Laboratories ACL Reference Emulsion

REAGENT PREPARATION:

Organon Teknika Auto aPTT reagent—Reconstituted with 6 ml Distilled water. Approximately equal amounts of phosphatidyl choline, phosphatidyl ethanolamine, and phosphatidyl serine. Stable up to 24 hours at 2°–8° C.

Enzyme Research laboratories APC—Ready for use.

Organon Teknika Factor V Deficient Plasma— Reconstitute each vial with 1.2 ml Distilled water. Allow to stand at room temperature for 20 minutes. swirl gently before use. Stable up to 8 hours at 2°–8° C.

Organon Teknika Simplastin Excel thromboplastin with CaCl$_2$—Allow the product to equilibrate to room temperature prior to reconstitution. Reconstitute with diluent provided. Let the product stand for 15 minutes. Shake vigorously to mix. Use within four days of reconstitution.

Calibration Plasma—Allow the product to equilibrate to room temperature prior to reconstitution. Reconstitute with 1 ml Distilled water and stand for 15 minutes. Swirl gently before use. Stable up to 8 hours at 2°–8° C.

Factor Frozen Pooled Normal and Abnormal Plasma— Thaw rapidly at 37° C. use immediately.

ACL Reference Emulsion—Ready for use. Stable at 25° C. till expiration date.

PROCEDURE:

1. Prepare two samples. Add 100 μl of patient plasma and 100 μl of Auto aPTT reagent into both samples and incubate at 37° C. for 5 minutes.
2. After 5 minutes, add 0.5 μl of distilled water to one sample and 0.5 μl of APC (1.18 mg/ml) to the other sample. Incubate both samples at 37° C. for 2 minutes.
3. At the end of the 2 minutes, add 250 μl of Factor Diluent to both samples and perform a Factor V assay in the ACL 3000+ instrument according to the manufacture's instructions. This results in a 1:3.5 plasma dilution. This dilution can be adjusted in the range from 1:2 to 1:20 to bring the measurements within the manufacturer's recommended measurement range for the instrument.

CALCULATION: FVR ratio=FV(%) without APC/FV (%) with APC

REFERENCE RANGE: The range obtained in 25 health controls with negative PCR for FV Leiden was 2.1 to 3.7. A value equal to or greater than 2.1 was considered to indicate a Factor V normal individual.

CONTROL PROCEDURE:

George King Fact Normal Pooled Plasma (George King Biomedical, Inc.)

George King B Fact abnormal Pooled Plasma

Chromogenix Abnormal Control Plasma

LIMITATIONS OF THE PROCEDURE: This test is not affected by the presence of lupus inhibitor antibodies or anticoagulant treatment. It is completely sensitive and specific for detection of the Factor V Leiden defect.

PCR GENETIC TESTING

Genetic testing for the Factor V Leiden defect (FVL) was performed by the polymerase chain reaction test (PCR), as described by Kirschenbaum and Foster in *Thrombosis and Hemostasis*, Vol. 74, (1995) Pp. 874–878.

RESULTS

Normal reference ranges of the ratios for the tests were produced by applying the three tests to plasma from 25 FVL negative control subjects. The reference ranges are: APCR—2.2 to 3.4, APCM—2.2 to 3.6, and FVR—2.1 to 3.7 (See Table 1A). The manufacturer's stated reference range for the commercial COATEST is 2.0–5. The following results are the product of application of the three tests to plasma from 110 patients. Because of a prolonged baseline aPTT, a definite clotting endpoint could not be obtained with the APCR test on 33 patients and with the APCM test on one patient. In all the plasma samples tested with the FVR, clotting endpoints were observed and the FVR ratio could be calculated. In most of the instances of poorly defined endpoint clotting times with the APCR and APCM the patients were on anticoagulants or had LI.

FACTOR V RATIO TEST RESULTS

Of the 110 patients tested, all those with a positive PCR genetic test for FVL had FVR ratios of 2.0 or less. 29 of the 34 patients with the FVL mutation had FVR ratios of 1.8 or less. There were no patients with negative PCR for FVL with a ratio less than 2.1. There were two FVL negative patients with an FVR ratio of 2.1. The FVR ratios for all the other FVL negative patients were greater than 2.2 (See FIG. 1). For the 37 patients receiving heparin and/or coumadin treatment, all patients that test positive for FVL had FVR ratios less than 2.1 and all patients that tested negative for FVL had FVR ratios greater than 2.1. Similarly, the presence of ACL and/or LI antibodies did not affect the specificity of the test results.

Plasma from a total of 24 patients with LI and/or ACL antibodies was tested. Of these 24 patients, 19 who were FVL negative, had FVR ratios 2.2 or greater, and 5 who were FVL positive, had ratios of 1.7 or less. This data, shown in Table 2 shows that the FVR test was 100% sensitive and specific for the FVL mutation and that anticoagulation treatment or the presence of LI/ACL antibodies did not alter the specificity or the sensitivity of the FVR assay. The 4 patients with homozygous FVL defect had FVR ratios of 1.1 or less (3 were 1.1 and one 1.0).

The FVR ratios of the heterozygous group ranged from 1.3 to 2.0 with a mean of 1.6+/−1 STD 0.2 (See table 1B.)

TABLE 1

A.

| CONTROL | N = 25 APCM RATIO | N = 25 APCR RATIO | N = 25 FVR RATIO |
|---|---|---|---|
| RANGE | 2.2–3.8 | 2.2–3.4 | 2.1–3.7 |
| MEAN | 3.0 | 2.8 | 2.9 |
| 1 STD | 0.4 | 0.3 | 0.4 |

B.

| | HETEROZYGOUS | | | HOMOZYGOUS | | |
|---|---|---|---|---|---|---|
| FVL(+) | N = 30 APCM | N = 22 APCR | N = 30 FVR | N = 4 APCM | N = 4 APCR | N = 4 FVR |
| RANGE | 1.1–2.3 | 1.3–3.3 | 1.2–2.0 | 1.1–1.5 | 1.2–1.6 | 1.1–1.1 |
| MEAN | 1.7 | 2.3 | 1.6 | 1.3 | 1.4 | 1.1 |
| 1 STD | 0.3 | 0.5 | 0.2 | 0.1 | 0.1 | 0.0 |

TABLE 1-continued

C.

| FVL(−) COUM. | N = 19 APCM RATIO | N = 7 APCR RATIO | N = 19 FVR RATIO |
|---|---|---|---|
| RANGE | 2.0–3.2 | 2.4–4.0 | 2.0–3.6 |
| MEAN | 2.6 | 3.2 | 2.8 |
| 1 STD | 0.3 | 0.4 | 0.4 |

D.

| FVL(−) ACL/LI | N = 16 APCM RATIO | N = 10 APCR RATIO | N = 17 FVR RATIO |
|---|---|---|---|
| RANGE | 1.7–3.7 | 1.3–3.7 | 2.1–3.7 |
| MEAN | 2.7 | 2.5 | 2.9 |
| 1 STD | 0.5 | 0.6 | 0.4 |

Table 1 (A–D) summarizes the range, mean and standard deviation of ratio measurements for the three tests: (a) for the control group of 25 FVL(−) individuals; (b) for individuals with heterozygous or homozygous FVL defect; (c) Factor V-normal individuals receiving coumadin therapy; and (d) for Factor V-normal individuals testing positive for ACL/LI antibodies.

APCR TEST RESULTS

FIG. 1 shows that the APCR ratio of plasma from 15 of 26 FVL positive patients was greater than 2.2 thus within the normal range shown in Table 1A. In 3 of 51 FVL negative patients the APCR ratio was than 2.2, therefore, below the normal range shown in Table 1A. The test could not be performed in 33 plasma samples (See FIG. 1.) Twenty of the 33 samples that could not be test were obtained from patients receiving anticoagulants, four samples had LI antibodies, five had LI antibodies and were receiving anticoagulation treatment, and four patients were receiving no anticoagulants and tested negative for ACL/LI antibodies. In plasma from 21 heterozygous FVL patients, the APCR ratios ranged from 1.3 to 3.3 with a mean of 2.3 (1 STD+/−0.5) (see table 1B). In plasma from the 4 homozygous FVL patients the APCR ratios ranged from 1.2 to 1.5. Although the APCR ratios of the 4 homozygous patients were generally lower than the APCR ratios of the heterozygous group, there was one heterozygous patient whose plasma tested with an APCR ratio of 1.3, overlapping the ratio of the homozygous group. One FVL negative patient had a ratio of 1.3, well below the normal range shown in Table 1A. APCR testing of plasma from 5 FVL positive patients not receiving anticoagulation treatment nor with ACL/LI antibodies resulted in APCR ratios greater than 2.2, within the normal range shown in Table 1A. For these five patients, the FVR ratio was 1.9 or less and the APCM ratio was 1.6 or less, appropriately below the normal range. The sensitivity and specificity of the APCR ratio for FVL were 42% and 94% respectively. (See Table 2.)

TABLE 2

A. APCR

| | APC-R (+) | APC-R (−) | | |
|---|---|---|---|---|
| FVL (+) | 11 | 15 | Sensitivity | 42% |
| FVL (−) | 3 | 48 | Specificity | 94% |
| | | | Positive predicted value | 78% |

TABLE 2-continued

|  |  |  |  |  |
|---|---|---|---|---|
|  |  |  | Negative predicted value | 76% |
|  |  |  | Not determined | 42% |

B. APCM

|  | APC-R (+) | APC-R (−) |  |  |
|---|---|---|---|---|
| FVL (+) | 33 | 1 | Sensitivity | 97% |
| FVL (−) | 3 | 72 | Specificity | 96% |
|  |  |  | Positive predicted value | 91% |
|  |  |  | Negative predicted value | 98% |
|  |  |  | Not determined | 1% |

C. FVR

|  | APC-R (+) | APC-R (−) |  |  |
|---|---|---|---|---|
| FVL (+) | 34 | 0 | Sensitivity | 100% |
| FVL (−) | 0 | 76 | Specificity | 100% |
|  |  |  | Positive predicted value | 100% |
|  |  |  | Negative predicted value | 100% |
|  |  |  | Not determined | 0% |

*APC-R denotes APC resistance

Table 2 summarizes the predictive value of the APCR, APCM and FVR tests for identification of FVL individuals. This table reports the sensitivity, specificity, positive predicted value, and negative predicted value for the three assay (APCR, APCM, and FVR). The "sensitivity" of each test is the number of FVL positive patients that tested as APC resistant, as a percentage of all FVL positive patients tested. The "specificity" of each test is the number of FVL-normal patients that tested APC normal, as a percentage of all FVL normal patients tested. The "positive predicted value" for each test is the number of FVL positive patients that tested APC resistant as a fraction of all patients that tested APC resistant. The "negative predicted value" is the number of FVL normal patients that tested APC normal as a percentage of all patients testing APC normal. The Table reports as "not determined," the percentage of patients whose plasma could not be tested by that assay.

APCM TEST RESULTS

The APCM ratio could not be obtained for one plasma sample. That patent tested positive for LI/ACL antibodies. One of the 34 FVL positive patients had an APCM ratio greater than 2.2 (3.1), within the normal range, and 3 of 75 FVL negative patients had APCM ratios of 2.1, below the normal range. (See FIG. 1.) One of the latter 3 patients was not receiving anticoagulants, nor did that patient positive for ACL/LI antibodies. APCM ratios for the heterozygous FVL group (29 patients) ranged from 1.1 to 2.3 with a mean of 1.7 (+/−1STD 0.3) (see table 1C). The 4 homozygous FVL patients had APCM ratios of 1.1 to 1.5. However, the APCM ratios of the homozygous patients overlapped with the APCM ratios of the heterozygous group. Plasma from the other 3 homozygous patients had APCM ratios below the APCM ratios for its heterozygous group of patients. The sensitivity and specificity of the APCM assay for the FVL defect were 97% and 96% respectively. (See Table 2.)

GENERAL TEST COMMENTS

Figure 2:
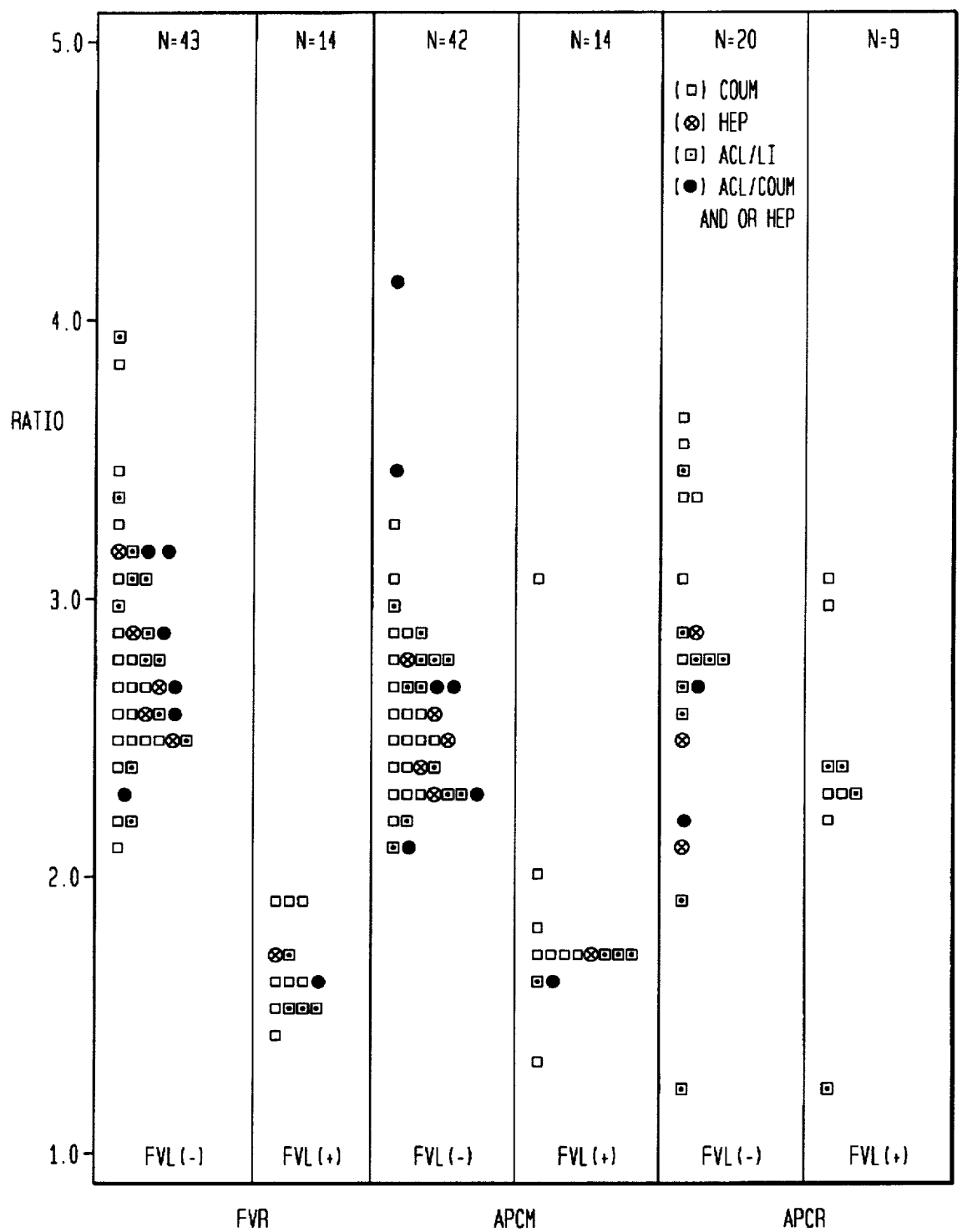
FIG. 2 is a chart showing the results of FVR ratio, APCM ratio, and APCR ratio measurements of plasma from individuals receiving coumadin or heparin therapy, individuals testing positive for lupus inhibitor/anticardiolipin antibodies, and individuals testing positive for anticardiolipin antibodies and receiving coumadin and/or heparin therapy. The test results for each test are indicated separately for Factor V-normal (FVL(−)) individuals and individuals with the Factor V Leiden defect (FVL(+)).

The effects of anticoagulation treatment and the presence of ACL/LI antibodies were noted in the above discussion of the APCR and APCM tests. (See FIG. 2). These results showed that for the APCR and APCM tests there were many patients whose plasma could not be tested. These tests showed many FVL negative patients (normal) whose ratios were below the range for normal individuals shown in Table 1A, and many FVL positive patients whose plasma showed ratios within the range for normal individuals. In the APCR test there was no reliable clotting endpoint for the plasma of 17 FVL negative patients and 5 FVL positive patients receiving coumadin. Seven of these patients had additional heparin treatment and/or tested positive for ACL/LI antibodies.

With the APCM test there was one ACL/LI patient in which the ratio could not be determined. APCR tests of plasma from 6 positive FVL patients receiving coumadin resulted in ratios from 2.2 to 3.1, within the normal range shown in Table 1A. FVL negative patients who tested positive for ACL/LI had APCR ratios of 1.9 and 1.3. In 3 FVL positive patients, testing positive for ACL/LI, the APCR ratio was 2.3 to 2.4, within the normal range. One FVL positive patient receiving coumadin had an APCM ratio of 3.1, within the normal range. Two FVL negative patients had APCM ratios of 2.1. One of those patients was receiving coumadin and was ACL/LI positive, and the other patient tested positive for ACL/LI antibodies. In two additional FVL negative patients, the test ratios were at the lower end of the control range. Of the 5 FVL negative patients on heparin, the FVR ratios ranged from 2.5 to 3.2, within the normal range. One FVL positive patient receiving heparin had a FVR ratio of 1.7, appropriately below the normal range.

In summary, there were 15 FVL positive patients in which the APCR assay gave false negative result (i.e., APCR ratio within the normal range). Most of these were the patients receiving anticoagulation (6 out of 15) or had LI and/or anticardiolipin antibodies (4 out of 15). In addition, APCR testing of three FVL negative patients gave a false positive result (i.e., APCR ratio below the normal range). The APCM assay showed an improved sensitivity and specificity. However, three FVL negative patients tested APCR positive and one FVL positive patient on coumadin had a normal APCR ratio (i.e., APCR negative). In contrast, using the FVR assay all 34 FVL positive patients had FVR ratios below the normal range and there were no FVL negative patients who had FVR ratios below the normal control range. This includes those patients with ACL/LI antibodies, and those receiving coumadin or heparin anticoagulation treatment.

COMPARISON TESTING

To assess the effect of the phospholipid incubation step, plasma samples were run through the FVR assay and through a similar test and without phospholipid incubation, but otherwise under identical conditions.

1) Four aliquot samples (2 sets) of test platelet poor plasma for each individual tested were run in parallel. One pair of the samples was run as in the FVR assay with 100 µl of one commercial aPTT phospholipid/contact activator reagent, and the other set of the samples were run with 100 µl of Factor Diluent™ in place of the phospholipid/contact activator reagent. The results were expressed as Factor V coagulant activity ratio.

TABLE 3

FV Level with Phospholipid/Silica Reagent

|  | FV% | FV% + APC |  | FVR |
|---|---|---|---|---|
|  | 72.0 | 33.0 | 39.0 | 2.2 |
|  | 63.0 | 28.0 | 35.0 | 2.3 |
| FV Leiden (−) | 106.0 | 38.0 | 68.0 | 2.8 |
| ACL/LI (−) | 129.0 | 56.0 | 73.0 | 2.3 |
| Coumadin (−) | 73.0 | 16.0 | 57.0 | 4.6 |
| N = 15 | 134.0 | 56.0 | 78.0 | 2.4 |

TABLE 3-continued

FV Level with Phospholipid/Silica Reagent

|  | FV% | FV% + APC | FVR |  |
|---|---|---|---|---|
|  | 139.0 | 46.0 | 93.0 | 3.0 |
|  | 150.0 | 41.0 | 109.0 | 3.7 |
|  | 129.0 | 48.0 | 81.0 | 2.6 |
|  | 91.0 | 38.0 | 53.0 | 2.4 |
|  | 111.0 | 45.0 | 66.0 | 2.5 |
|  | 103.0 | 41.0 | 62.0 | 2.5 |
|  | 123.0 | 47.0 | 76.0 | 2.6 |
|  | 81.0 | 29.0 | 52.0 | 2.8 |
|  | 97.0 | 37.0 | 60.0 | 2.6 |
| MEAN | *106.7 | **39.9 | ***66.8 | 2.8 |
| 1 STD | 27.0 | 10.7 |  | 0.6 |
| FV Leiden (−) | 87.0 | 40.0 | 47.0 | 2.2 |
| ACL/LI (+) | 136.0 | 47.0 | 89.0 | 2.9 |
| N = 5 | 113.0 | 41.0 | 72.0 | 2.8 |
|  | 91.0 | 40.0 | 51.0 | 2.3 |
|  | 114.0 | 46.0 | 68.0 | 2.5 |
| MEAN | 108.2 | 42.8 | 65.4 | 2.5 |
| 1 STD | 19.8 | 3.4 | 17.0 | 0.3 |
| FV Leiden (+) | 147.0 | 84.0 | 63.0 | 1.8 |
| ACL/LI (−) | 123.0 | 75.0 | 48.0 | 1.6 |
| N = 5 | 90.0 | 60.0 | 30.0 | 1.5 |
|  | 157.0 | 84.0 | 73.0 | 1.9 |
|  | 97.0 | 55.0 | 42.0 | 1.8 |
| MEAN | 122.8 | 71.6 | 51.2 | 1.7 |
| 1 STD | 29.6 | 13.5 | 17.0 | 0.2 |

FV Level without Phospholipid/Silica Reagent

|  | FV% | FV% + APC | FVR |  |
|---|---|---|---|---|
|  | 70.0 | 48.0 | 22.0 | 1.4 |
|  | 57.0 | 44.0 | 13.0 | 1.3 |
| FV Leiden (−) | 101.0 | 61.0 | 40.0 | 1.7 |
| ACL/LI (−) | 117.0 | 85.0 | 32.0 | 1.4 |
| Coumadin (−) | 73.0 | 39.0 | 34.0 | 1.9 |
| N = 15 | 123.0 | 75.0 | 48.0 | 1.6 |
|  | 103.0 | 57.0 | 46.0 | 1.8 |
|  | 136.0 | 76.0 | 60.0 | 1.8 |
|  | 102.0 | 58.0 | 44.0 | 1.7 |
|  | 73.0 | 57.0 | 16.0 | 1.3 |
|  | 93.0 | 53.0 | 40.0 | 1.8 |
|  | 103.0 | 61.0 | 42.0 | 1.7 |
|  | 105.0 | 65.0 | 40.0 | 1.6 |
|  | 75.0 | 42.0 | 33.0 | 1.8 |
|  | 90.0 | 65.0 | 35.0 | 1.4 |
| MEAN | *94.7 | **59.1 | ***36.3 | 1.6 |
| 1 STD | 21.9 | 13.0 | 12.3 | 0.2 |
| FV Leiden (−) | 63.0 | 41.0 | 22.0 | 1.5 |
| ACL/LI (+) | 118.0 | 62.0 | 56.0 | 1.9 |
| N = 5 | 108.0 | 62.0 | 46.0 | 1.7 |
|  | 64.0 | 38.0 | 26.0 | 1.7 |
|  | 101.0 | 67.0 | 34.0 | 1.5 |
| MEAN | 90.8 | 54.0 | 36.8 | 1.7 |
| 1 STD | 25.6 | 13.4 | 14.1 | 0.2 |
| FV Leiden (+) | 147.0 | 108.0 | 39.0 | 1.4 |
| ACL/LI (−) | 102.0 | 89.0 | 13.0 | 1.1 |
| N = 5 | 87.0 | 72.0 | 15.0 | 1.2 |
|  | 118.0 | 105.0 | 13.0 | 1.1 |
|  | 87.0 | 69.0 | 18.0 | 1.3 |
| MEAN | 108.2 | 88.6 | 19.6 | 1.2 |
| 1 STD | 25.2 | 18.1 | 11.0 | 0.1 |

*p < 0.05  p < 0.05  *p < 0.05   Paired t-test

Table 3 compares the results of a series of FVR tests and a parallel series of tests run under identical conditions, but without a phospholipid/contact activator reagent, for: (a) 15 individuals who were Factor V-normal, who tested negative for ACL/LI antibodies and were receiving no anticoagulant therapy; (b) 5 individuals who were Factor V-normal, but tested positive for ACL/LI antibodies; and (c) 5 individuals who tested positive for the FVL defect, but negative for ACL/LI antibodies.

In table 3 are the results of the assessment of the effect of the inclusion of a phospholipid/contact activator step in the FVR assay. The plasmas from 15 FVL negative subjects, who tested negative for ACL/LI antibodies and were not receiving anticoagulants were utilized. The FVR assay with a phospholipid/contact activator reagent step was performed and a similar assay using an inert reagent was also performed on these 15 FVL negative plasma samples. The mean FVR ratio with the phospholipid/contact activator material was 2.8 (+/−1STD 0.6) and the mean ratio for the test with inert reagent was 1.6 (+/−1STD 0.2). The differences of the mean ratios between the phospholipid/contact activator and non phospholipid/contact activator samples were statically significant. (See Table 3.) When 5 FVL negative, ACL/LI positive patients were assessed in the same manner, the mean FVR ratio with the phospholipid material was 2.5 (+/−1STD 0.3), within the normal range, and without phospholipid/contact activator the mean ratio was 1.5 (+/−1STD 0.2), below the normal range. When plasma samples from 5 FVL positive patients were studied in the same manner, the phospholipid treated samples had a mean FVR ratio of 1.7 (+/−1STD 0.2). Without phospholipid, the mean ratio was 1.2 (+/−1STD 0.1). These findings establish that incubation with the phospholipid contact activator reagent neutralizes the effect of the LI/ACL antibodies and increases the difference between the FVR ratio of FVL positive and FVL negative patients, making a clearer distinction between patients with and without the FVL defect.

2) A set of tests was run to compare the effect of the use of other phospholipid/contact activator (silica or kaolin) preparations on the FVR assay. To make the comparison, the FVR assay was performed with 4 phospholipid preparations found in commercial aPTT reagents, a Factor Diluent™, and a contact activator alone (kaolin suspension). One of the commercial aPTT reagents, AutoaPTT, is the same reagent used as described above. 12 aliquot samples (6 sets) of test platelet poor plasma were run in parallel. The assays were run identically to the FVR except 100 μl of Auto aPTT, Pathromtin, Kaolin, Factor Diluent, Plateletlysate, and SynthASIL™. The aPTT reagents were used in the same dilutions as recommended by the supplier for the standard aPTT assay.

TABLE 4

| Reagent 1 AutoaPTT (Organon Teknika) | | | |
|---|---|---|---|
| FV% | FV% + APC | | FVR |
| 81.0 | 22.0 | 59.0 | 3.7 |
| 97.0 | 44.0 | 53.0 | 2.2 |
| 87.0 | 38.0 | 49.0 | 2.3 |
| 97.0 | 37.0 | 60.0 | 2.6 |
| 72.0 | 29.0 | 43.0 | 2.5 |
| MEAN 86.8 | 34.0 | 52.8 | 2.7 |
| Reagent 2 SynthASil aPTT (Hemoliance) | | | |
| 123.0 | 32.0 | 91.0 | 3.8 |
| 123.0 | 53.0 | 70.0 | 2.3 |
| 118.0 | 54.0 | 64.0 | 2.2 |
| 109.0 | 61.0 | 48.0 | 1.8 |
| 109.0 | 47.0 | 62.0 | 2.3 |
| MEAN 116.4 | 49.4 | 67.0 | 2.5 |
| Reagent 3 Pathromatin aPTT (Behring Diagnostic Inc.) | | | |
| 76.0 | 15.0 | 61.0 | 5.1 |
| 101.0 | 27.0 | 74.0 | 3.7 |
| 101.0 | 39.0 | 62.0 | 2.6 |
| 84.0 | 33.0 | 51.0 | 2.5 |
| 94.0 | 30.0 | 64.0 | 3.1 |
| MEAN 91.2 | 28.8 | 62.4 | 3.4 |

TABLE 4-continued

Reagent 1 AutoaPTT (Organon Teknika)

| FV% | FV% + APC | | FVR |
|---|---|---|---|
| Reagent 4 Phospholipid (American Biproduct) | | | |
| 70.0 | 42.0 | 28.0 | 1.7 |
| 94.0 | 61.0 | 33.0 | 1.5 |
| 80.0 | 62.0 | 18.0 | 1.3 |
| 84.0 | 59.0 | 25.0 | 1.4 |
| ND | ND | ND | ND |
| 82.0 | 56.0 | 26.0 | 1.5 |
| Reagent 5 Factor Diluent (Instrumentation Lab) | | | |
| 84.0 | 47.0 | 37.0 | 1.8 |
| 101.0 | 61.0 | 40.0 | 1.6 |
| 97.0 | 83.0 | 14.0 | 1.2 |
| 90.0 | 65.0 | 25.0 | 1.4 |
| 87.0 | 63.0 | 24.0 | 1.4 |
| 91.8 | 63.8 | 28.0 | 1.5 |
| Reagent 6 Kaolin (Behring Diagnostic Inc.) | | | |
| 105.0 | 59.0 | 46.0 | 1.8 |
| ND | ND | ND | ND |
| 109.0 | 65.0 | 44.0 | 1.7 |
| 109.0 | 55.0 | 54.0 | 2 |
| 101.0 | 53.0 | 48.0 | 1.9 |
| 106.0 | 58.0 | 48.0 | 1.9 |

Table 4 summarizes the results of a series of FVR tests (and FVR-parallel tests run on 5 Factor V-normal (FVL(−)) plasma samples using six different reagents in the first incubation step. Reagents 1–4 are commercial phospholipid preparations. Reagent 4 being prepared without a contact activator. Reagent 5 is Factor Diluent, and Reagent 6 is a kaolin suspension.

In table 4 are the results of this assessment of four commercially available phospholipid aPTT reagents and kaolin alone, run in accordance with the FVR assay procedure. Reagents 1 and 2 consist of phospholipid, with silica as the contact activator substance. Reagent 3 is phospholipid with kaolin as the contact activator substance. Reagent 4 contains phospholipid, without a contact activator substance. Reagent 6 is kaolin alone. Reagent 5 is Factor Diluent™ without phospholipid or a contact activator substance. Reagents 1 through 4 are commercially prepared reagents for the aPTT based clotting test. When Reagents 1, 2, and 3 are used in the FVR test, of the 5 FVL negative plasma samples all produced FVR ratios of 2.5 or greater, within the normal range. With reagents 4 and 6 the FVR ratios were 1.5 and 1.9 respectively, below the normal range. Without either phospholipid or an activating substance the ratio was similar to that demonstrated in the above comparison of the FVR test with the similar test without phospholipid. The increase in the FVR ratio noted using the reagents containing both phospholipid and a contact activator substance (Reagents 1, 2, and 3) over the ratios obtained with reagents without both constituents (reagents 4, 5, and 6) are due to greater degree of FVa degradation by APC. The difference of FVR noted in the group of reagents containing both phospholipid and activator substance may due to the composition and/or sources of these substances. However, all ratios were within the normal range.

The incorporation of phospholipid/contact activator in the FVR assay acts to neutralize the inhibitory effect of LI antibodies on the APC degradation of factor Va. The utility of a phospholipid with either silica or kaolin is demonstrated by the data shown in table 4. The three reagents which contained phospholipid and either silica or kaolin had greater degree of degradation of Factor Va by APC and higher FVR ratio than obtained with phospholipid or kaolin alone (reagents 4 and 6). The resultant ratios with reagents 4 and 6 were closer to the FVR obtained without either phospholipid or activating substances (reagent 5). These results would support the proposition that phospholipid preparations with a contact activator provide a surface for enhanced APC activity. The specific composition of the phospholipid reagent is a factor in the reaction as demonstrated by the modest differences in the effects produced by reagents 1, 2, and 3. However, these test results demonstrate that these differences do not affect the ability of the FVR assay to differentiate between FVL-positive and FVL-negative individuals. In conclusion these results show that the tissue factor-based Factor V assay system with the additional step of incubation with phospholipid/silica, the FVR assay, is an unexpectedly more reliable method of detecting the FVL mutation than the prior art methods.

The effect of including a phospholipid/contact activator reagent in the FVR assay system is demonstrated in table 3, comparing the FVR test results with the results of a Factor V assay based test that does not include a phospholipid/contact activator incubation step. The difference in the FVR ratio for 15 FVL negative subjects with and without the inclusion of a phospholipid/contact activator incubation step was statistically significant ($p<0.005$). The factor V coagulant activity levels with inclusion of a phospholipid/contact activator incubation step before the addition of APC, were higher than in the non-phospholipid/contact activator group, and there is a greater degree of factor Va degradation with exposure to phospholipid/contact activator reagent. ($p<0.005$) These findings suggest that the phospholipid/contact activator reagent enhances the degradation of factor Va by APC.

The effects of anionic phospholipids in the APCR test (Coatest™) were assessed by Luddington et al. (British Journal of Hematology, Vol. 92 (1996) 744). They were concerned that platelet contamination might result in apparent APC resistance, since the assembly of the prothrombinase complex and the inactivation of factor V are modulated on anionic phospholipid surfaces. It was postulated that the platelet anionic surface upon which APC degradation of factor Va is enhanced might be countered by the increased prothrombinase activity which is promoted on the platelet phospholipid surface. Therefore the combination of these opposing activities might result in the increased generation of thrombin and result in what appears to be increased resistance to APC. Others have addressed this issue in the use of freeze-thawed plasma samples and the subsequent effect of anionic phospholipid from the disrupted platelets. Almost 95% of the specimens in our assay were frozen-thawed after separation of plasma by vigorous centrifugation and filtration. We noted no difference in the FVR test results when frozen specimens were compared fresh specimens, the FVR assay remained unaffected in differentiating between positive and negative FVL patients.

The FVR test results demonstrate that the additional step of incubating with a phospholipid/contact activator reagent, before the addition of APC, neutralized the effect of lupus inhibitor or anticardiolipin antibodies. This was demonstrated by analysis of 5 plasma samples from FVL negative patients who tested positive for lupus inhibitor and/or anticardiolipin antibodies. The FVR assay, including a phospholipid/contact activator step, was performed together with a parallel assay using an inert reagent in place of the phospholipid/silica reagent. The test ratios without phospholipid/silica were very close to the test ratios for 5 samples tested in the same manner from FVL positive patients. Use of the phospholipid/silica incubation step clearly separated the FVL negative patients from those with LI antibodies.

What is claimed is:

1. A method for identifying a patient at risk of a thrombotic disorder due to a Factor V defect, comprising:
   (a) incubating a test plasma with a first reagent comprising a phospholipid composition and a contact activator;
   (b) adding a second reagent comprising activated protein C to a first aliquot of the test plasma but not to a second aliquot of the test plasma and incubating the first aliquot and the second aliquot;
   (c) measuring the Factor V activity of the plasma in the first aliquot and in the second aliquot in the presence of Factor V depleted plasma and thromboplastin;
   (d) determining a ratio of the Factor V activity of the second aliquot to the Factor V activity of the first aliquot; and
   (e) determining whether the ratio is above or below a predetermined threshold value, wherein a ratio below the predetermined threshold value identifies a patient with the Factor V defect.

2. The method of claim 1 in which the phospholipid composition is a naturally derived phospholipid, a synthetic phospholipid, or a combination thereof.

3. The method of claim 2 in which the phospholipid composition consists of approximately equal amounts of phosphatidyl choline, phosphatidyl ethanolamine, and phosphatidyl serine.

4. The method of claim 1 in which the phospholipid composition constitutes from 0.25 micrograms to 75 micrograms per 100 microliter portion of the first reagent.

5. The method of claim 1 in which the contact activator is at least one member selected from the group consisting of micronized silica, kaolin, celite, and ellagic acid.

6. The method of claim 1 in which, during the measuring step, the plasma constitutes from a 1:2 to a 1:20 dilution in the remaining constituents, including an inert diluent solution.

7. The method of claim 1 in which the step of measuring the Factor V activity of the first aliquot and the Factor V activity of the second aliquot comprises the steps of:
   (a) adding Factor V deficient plasma to the first aliquot and to the second aliquot;
   (b) adding a third reagent comprising thromboplastin and a compound containing $Ca^{2+}$ ions to the first aliquot and to the second aliquot, to initiate clotting; and
   (c) measuring the clotting time of the first aliquot and the clotting time of the second aliquot.

8. The method of claim 7 in which the Factor V deficient plasma is present in an amount at least equal to the amount of test plasma in the first aliquot and in the second aliquot.

9. A method of claim 1 in which the step of measuring the Factor V activity of the first aliquot and the Factor V activity of the second aliquot comprises:
   (a) adding a quantity of Factor V deficient plasma to the first aliquot and to the second aliquot;
   (b) adding a chromogenic substrate sensitive to a serine protease generated by Factor V activity;
   (c) adding thromboplastin to initiate the chemical reactions of the extrinsic portion of the clotting cascade; and
   (d) measuring the color change of the first aliquot and the color change of the second aliquot produced by reaction of the serine protease with the chromogenic substrate.

10. The method of claim 1 in which the predetermined threshold value of the ratio of Factor V activities is determined by testing plasma obtained from a control group of Factor V-normal individuals.

11. A kit comprising a set of reagents standardized to determine whether a patient is at risk of a thrombotic disorder due to a Factor V defect, said set of reagents comprising:
    (a) a first reagent comprising a phospholipid composition and a contact activator;
    (b) a second reagent comprising activated protein C;
    (c) a third reagent comprising Factor V deficient plasma; and
    (d) a fourth reagent comprising thromboplastin with $Ca^{2+}$.

12. The kit of claim 11 in which the activating composition comprises a phospholipid compound and a contact activator.

13. The kit of claim 12 in which the contact activator is at least one member of the group consisting of micronized silica, kaolin, celite, and ellagic acid.

14. A kit for determining whether a patient is at risk of a thrombotic disorder due to a Factor V defect, by a method comprising: (a) incubating the plasma with a reagent comprising a phospholipid composition and a contact activator; (b) adding activated protein C to one of two plasma portions; and (c) measuring the Factor V activity of each of the two plasma portions in the presence of Factor V depleted plasma and thromboplastin;
    wherein the kit comprises, in combination, a set of reagents standardized to determine whether a blood plasma sample contains a Factor V defect that places the patient at risk of a thrombotic disorder, comprising:
    (a) a first reagent comprising a phospholipid composition and a contact activator;
    (b) a second reagent comprising activated protein C;
    (c) a third reagent comprising Factor V depleted plasma; and
    (d) a fourth reagent comprising thromboplastin with $Ca^{2+}$.

15. A kit for determining whether a patient is at risk of a thrombotic disorder due to a Factor V defect by a method comprising: (a) incubating the plasma with a reagent comprising a phospholipid and a contact activator; (b) adding activated protein C to one of two plasma portions; (c) measuring the Factor V activity of each of the two plasma portions in the presence of Factor V depleted plasma and thromboplastin; wherein the kit comprises, in combination, a set of reagents standardized to determine whether a blood plasma sample contains a Factor V defect that places the patient at risk of a thrombotic disorder, comprising:
    (a) a first reagent comprising a phospholipid composition and a contact activator;
    (b) a second reagent comprising activated protein C;
    (c) a third reagent comprising Factor V depleted plasma;
    (d) a fourth reagent comprising thromboplastin in the absence of $Ca^{2+}$; and
    (e) a fifth reagent comprising a chromogenic substrate sensitive to a serine protease generated by Factor V activity.

* * * * *